US00PP23729P3

(12) United States Plant Patent
Bourne

(10) Patent No.: US PP23,729 P3
(45) Date of Patent: Jul. 9, 2013

(54) ***DIANTHUS* PLANTED NAMED 'WP10 HEL01'**

(50) Latin Name: *Dianthus×hybrida*
Varietal Denomination: WP10 HEL01

(76) Inventor: Carolyn Grace Bourne, Dawlish (GB)

( * ) Notice: Subject to any disclaimer, the term of this patent is extended or adjusted under 35 U.S.C. 154(b) by 191 days.

(21) Appl. No.: 13/134,777

(22) Filed: Jun. 14, 2011

(65) Prior Publication Data

US 2011/0321206 P1 Dec. 29, 2011

(51) Int. Cl.
*A01H 5/00* (2006.01)

(52) U.S. Cl.
USPC ..... Plt./279; Plt./272

(58) Field of Classification Search
USPC ..... Plt./272, 279
See application file for complete search history.

*Primary Examiner* — Susan McCormick Ewoldt

(57) ABSTRACT

A new cultivar of *Dianthus* plant named 'WP10 HEL01' which is characterized by compact mounding plant habit, silver-gray foliage and fragrant semi double flowers which are pure white in color with a deep cherry eye. In combination, these characteristics set 'WP10 HEL01' apart from all other existing varieties of *Dianthus* known to the inventor.

2 Drawing Sheets

Genus: *DIANTHUS.*
Species: ×*hybrida.*
Denomination: 'WP10 HEL01'.

BACKGROUND OF THE INVENTION

This application claims the benefit of priority under 35 U.S.C. 119(f) of the application for a grant of European Community Plant Breeders Rights which was filed for the instant plant variety on Jun. 25, 2010, Application Number 2010/1268.

The present invention relates to a new and distinct cultivar of hardy *Dianthus,* also known as garden pink, which is grown for use as a flowering plant for pots and containers and for planting in the garden and landscape. The new cultivar is known botanically as *Dianthus×hybrida* and will be referred to hereinafter by the cultivar name 'WP10 HEL01'.

'WP10 HEL01' is a complex hybrid plant that is the product of a long term breeding program conducted by the inventor in a cultivated area of Houndspool, Dawlish, Devon, United Kingdom. The inventor selected 'WP10 HEL01' in 2001 for its fragrant flowers which are semi-double and pure white in color with a deep cherry red eye, and also for its contrasting foliage. The foliage of 'WP10 HEL01' is markedly silver-gray in color.

'WP10 HEL01' was selected from seedlings raised by the inventor using seed which resulted from the open pollination of *Dianthus* 'Mendlesham Minx' (unpatented) as female parent plant. The inventor had deliberately exposed 'Mendlesham Minx' to open pollination by placing 'Mendlesham Minx' within a collection of the inventor's unreleased and unpatented seedlings during their flowering period.

'WP10 HEL01' is distinguishable from the female parent as follows: The habit of the female parent is more spreading, whereas 'WP10 HEL01' has a compact mounding habit. The flowers of the female parent are single, maroon in color with a white edge and flecks of white overall, whereas the flowers of 'WP10 HEL01' are semi-double and white in color with a deep cherry eye. The foliage of the female parent is blue-green as is typical of the genus *Dianthus,* whereas the foliage of 'WP10 HEL01' is silver-gray in color.

'WP10 HEL01' cannot be described in comparison with the unknown male parent.

The variety of *Dianthus* which is considered by the inventor to most closely resemble 'WP10 HEL01' is *Dianthus* 'BRILLIANT STAR' (U.S. Plant Pat. No. 13,025). 'BRILLIANT STAR' is distinguishable from 'WP10 HEL01' as follows: Mature plants of 'BRILLIANT STAR' are approximately 2.5 cm shorter in height than plants of 'WP10 HEL01'. 'BRILLIANT STAR' has a more compact habit with flowers borne on shorter stems. The foliage of 'BRILLIANT STAR' is blue green in color. In addition, the flowers of 'WP10 HEL01' are larger and more double compared to the flowers of "BRILLIANT STAR'.

Asexual reproduction of 'WP10 HEL01' was first accomplished by the inventor in 2001 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'WP10 HEL01'. These traits in combination distinguish this cultivar from all other commercial varieties known to the inventor. 'WP10 HEL01' has not been tested under all possible conditions and phenotypic differences may be observed with variations in environmental, climatic and cultural conditions, however, without any variance in genotype.

1. *Dianthus* 'WP10 HEL01' exhibits a compact mounding habit.
2. The flowers of *Dianthus* 'WP10 HEL01' are semi double.
3. The flowers of *Dianthus* 'WP10 HEL01' are pure white in color with a deep cherry eye.
4. *Dianthus* 'WP10 HEL01' blooms from April through October.
5. *Dianthus* 'WP10 HEL01' exhibits glaucous silver-gray foliage.

6. At eight months of age, the height of the foliage mound of *Dianthus* 'WP10 HEL01' is 22 cm to 28 cm, and the width is 15 cm to 20 cm.
7. *Dianthus* 'WP10 HEL01' is perennial and is hardy to −15° C.
8. *Dianthus* 'WP10 HEL01' is suitable for use as a flowering plant in pots and containers.

BRIEF DESCRIPTION OF THE DRAWINGS

The accompanying color drawings illustrate the overall appearance of the new *Dianthus* variety 'WP10 HEL01' showing colors as true as it is reasonably possible to obtain in colored reproductions of this type. Colors in the drawings may differ from the color values cited in the detailed botanical description, which accurately describe the actual colors of the new variety 'WP10 HEL01'.

The drawing labeled as FIG. 1 depicts an entire flowering plant.

Figure 1:
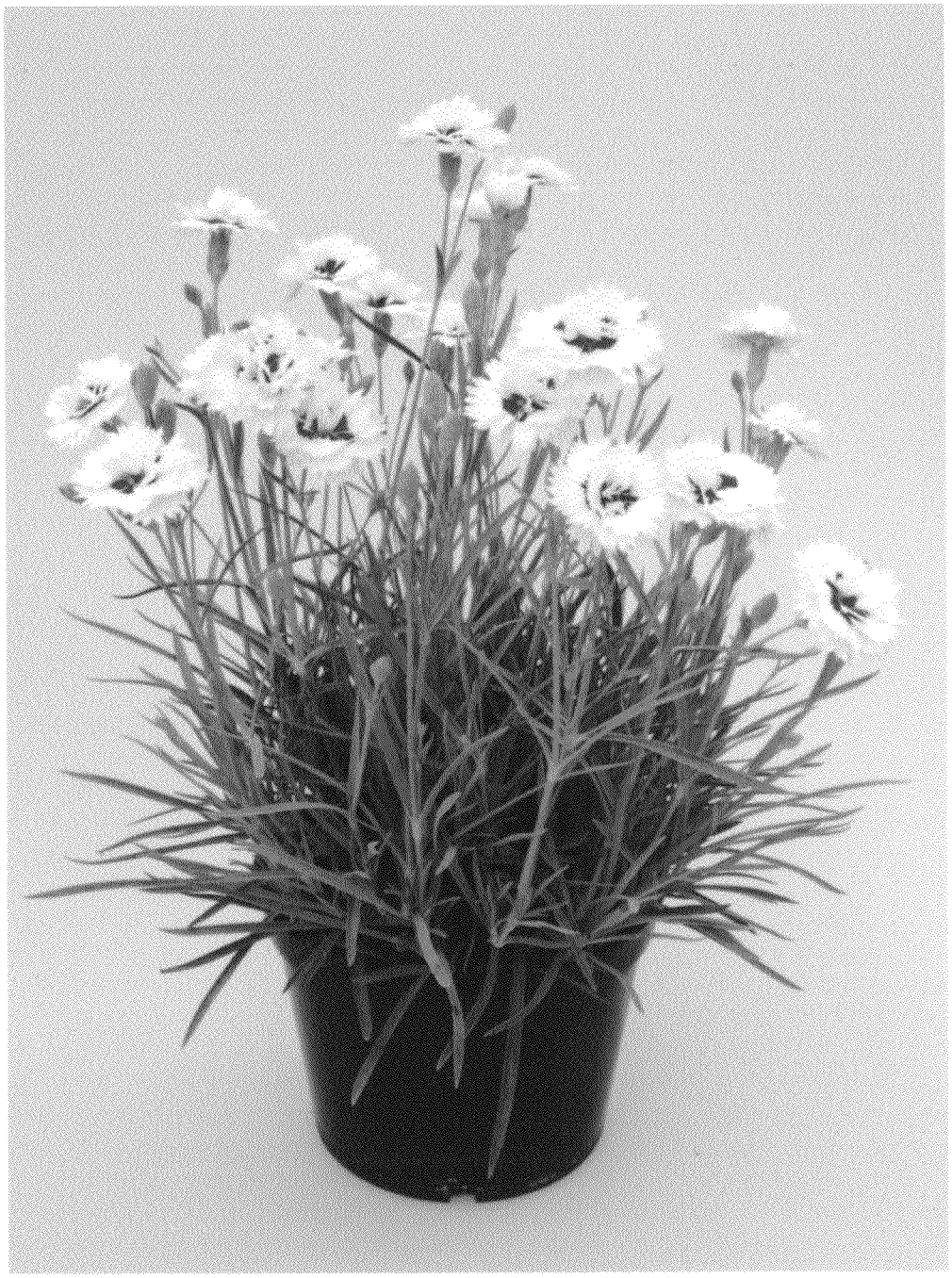
Figure 2:
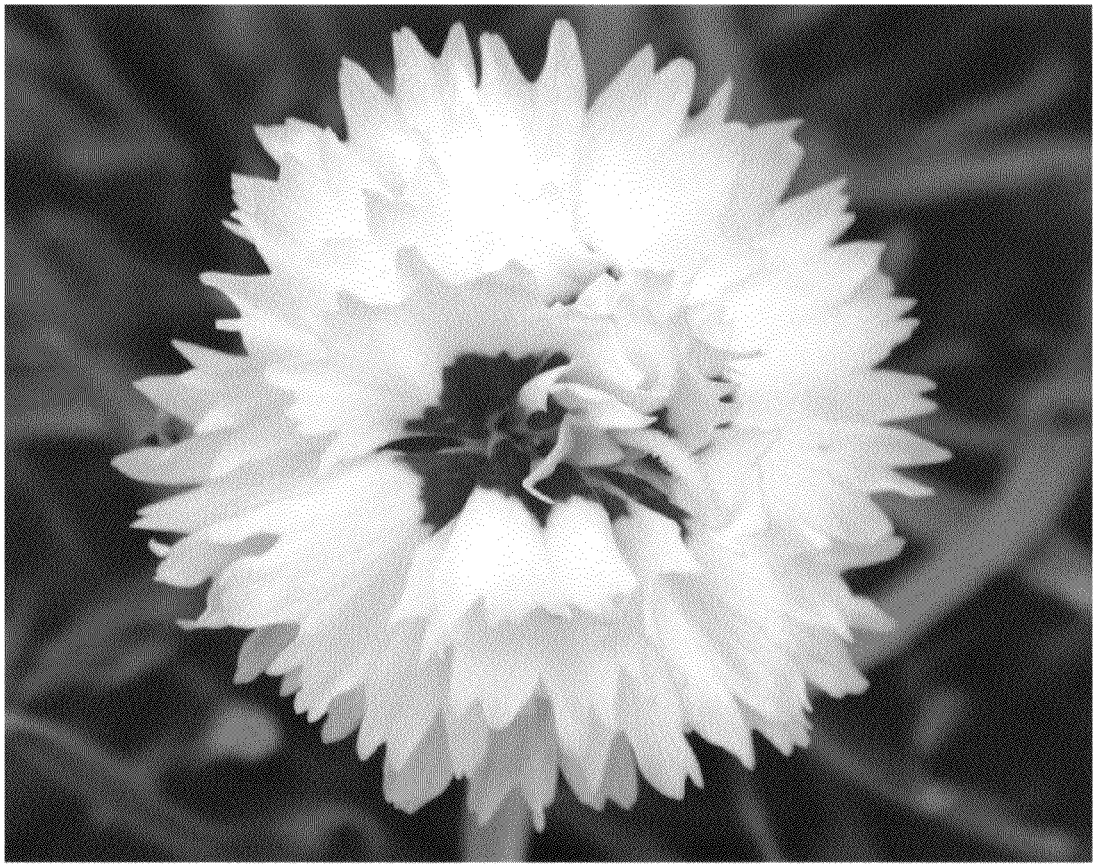

The drawing labeled as FIG. 2 depicts a close-up view of the flower.

All drawings were made of 9 months old plants which have been grown in 1.5-litre containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP10 HEL01'. Data was collected in spring from 1.5-litre container plants, and grown indoors in Devon, United Kingdom. The color determinations are in accordance with the 2002 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical: Classification:
Family: Caryophyllaceae.
Genus: *Dianthus*.
Species: ×*hybrida*
Denomination: 'WP10 HEL01'.
Parentage: A complex *Dianthus* hybrid that resulted from open pollination as follows.
Female parent: *Dianthus* 'Mendlesham Minx' (unpatented).
Male parent: Unknown.
Plant type: Flowering perennial.
Use of plant: As a flowering plant in containers, window boxes, planters, pots and the garden.
Bloom period: April-October in Devon, UK.
Plant habit: A compact mound with many branches and stems upright.
Height of plant: 22 cm to 28 cm after 8 months.
Width of plant: 15 cm to 20 cm after 8 months.
Hardiness: Has survived in temperatures of minus 15 Centigrade in Devon, United Kingdom. Early trials in the United States indicate survival in USDA Hardiness Zone 5.
Root system: Many fibrous roots.
Propagation method: Vegetative stem cuttings.
Cultural requirements: Grow in full sun, in well drained and moderately fertile soil, keep well fertilized and watered.
Diseases and pests: No particular resistance or susceptibility to *Dianthus* diseases and pests are known to the inventor.
Time to root cuttings: 10-14 days are required to produce roots on a vegetative cutting at the recommended temperatures.
Recommended temperature for rooting: A minimum of 15° C. air temperature and 21° C. base temperature at root level is required to produce roots on the cuttings.
Facilities for rooting: Mist propagation unit is required for satisfactory rooting of cuttings.
Crop time (from planting a rooted cutting): 3 months starting in the Spring and 6 months starting in the Fall.
Plant stem:
- *Shape.*—Cylindrical.
- *Length.*—15 to 20 cm.
- *Diameter.*—2 mm in diameter.
- *Surface.*—Glabrous and glaucous.
- *Color.*—188B.
- *Branching.*—Numerous shoots from the axils of the lower leaves.
- *Internode distance.*—From 10 mm (lowest internode) to 80 mm (uppermost internode).
- *Node dimensions.*—3 mm in diameter and 3 mm in length.

Leaf:
- *Type.*—Evergreen.
- *Shape.*—Linear.
- *Division.*—Simple.
- *Apex.*—Acute.
- *Base.*—Decurrent.
- *Venation.*—Not prominent.
- *Margins.*—Entire.
- *Arrangement.*—Opposite and spiraling on stem.
- *Attachment.*—Sheathing.
- *Surface* (*adaxial and abaxial*).—Glaucous.
- *Stipules.*—Absent.
- *Fragrance.*—Absent.
- *Dimensions.*—Length: 7 cm to 8 cm. Width: 3 mm.
- *Color.*—Adaxial surface: 189B. Abaxial surface: 189B.

Inflorescence:
- *Flower stem.*—Length: 15 cm-20 cm. Width: 2 mm. Stem strength: Erect. Stem color: 188B.
- *Inflorescence.*—Cymose.
- *Type.*—Salviform, symmetrical.
- *Development.*—Singly, in sequence commencing with the uppermost bud.

Buds:
- *Shape.*—Cylindrical.
- *Dimensions.*—16 mm in length and 6 mm in width.
- *Color.*—191B.
- *Surface texture.*—Glabrous.

Flowers:
- *Number.*—3 to 5 per stem.
- *Pedicel dimensions.*—15 cm to 20 cm in length and 2 mm in width.
- *Pedicel strength.*—Erect.
- *Pedicel color.*—188B.
- *Flower dimensions.*—Length (including calyx): 30 mm. Diameter: 36 mm.
- *Flower shape.*—Circular.

Flower profile: Reflexed.
- *Lastingness.*—10 days at 20° C., on the plant.
- *Fragrance.*—Moderate to strong, floral.
- *Flowering period.*—April to October, in Devon, UK.

Corolla:

*Shape* (*upper part of corolla*).—Convex.

*Shape* (*lower part of corolla*).—Flat convex.

*Petal arrangement.*—Persistent, apopetalous, overlapping.

*Petal margin.*—Crenate-dentate to serrate.

*Indentation.*—Varies between 0 mm and 3 mm.

*Petal texture.*—Soft.

*Flower type.*—Semi double.

*Petal number.*—20 to 25 true petals.

*Petal dimension.*—Length: 29 mm. Width: 18 mm.

*Color pattern.*—Blade is white with a maroon eye. Delicate pink flush in the white section of petal that disappears as the flower ages.

*Color of upper surface.*—Ground color of blade: White. Color of band across blade: 59A. Color of middle of strap: 145C. Color of base of strap: 145D.

*Color of lower surface.*—Ground color of blade: White. Color of middle of strap: 145C. Color of base of strap: 145D.

*Petal shape.*—Obdeltoid.

*Petal apex.*—Fan shaped.

*Petal base.*—Strap shaped, tapering towards base.

*Petal surface.*—Glabrous.

Calyx:

*Shape.*—Cylindrical.

*Sepal apex.*—Subacute.

*Sepal base.*—Fused.

*Longitudinal profile.*—Flat, parallel sides.

*Dimensions.*—Length: 17 mm. Diameter: 7 mm.

*Sepals.*—Fused to 4 mm below the subacute apex.

*Sepals.*—5 in number.

*Sepals color, outer surface.*—191B.

*Sepals color, inner surface.*—144B.

*Anthocyanin.*—Lightly present.

*Splitting.*—Not observed.

Epicalyx:

*Bracts number.*—1 pair of two.

*Shape of outer lobe.*—Acute.

*Dimensions.*—Width: 8 mm. Length: 6 mm.

*Color.*—N138D.

*Anthocyanin.*—Occasionally very lightly present.

Bracteoles:

*Number.*—1 pair of two.

*Dimensions.*—Width: 9 mm. Length: 9 mm.

*Color.*—N138D.

*Anthocyanin.*—Present occasionally — hue weak.

Reproductive organs:

*Stamens.*—Number: 0-5.

*Filaments.*—Number: 0 to 5. Color: White.

*Dimensions.*—Length: 20 mm in length and 0.5 mm in width.

*Anthers.*—Number: 0 to 5. Color: White. Length: 2 mm; diameter: 1 mm. Attachment: Dorsifixed.

*Pollen*—Occasionally present.

*Pollen color.*—11D.

*Style.*—Number: 2. Shoulder: Absent. Color: White. Length: 20 mm. Width: 1 mm.

*Stigma.*—Number: Single. Color: White. Dimensions: 20 mm when mature.

*Ovary.*—Position: Superior. Dimensions: Length: 9 mm. Diameter: 3 mm. Shape: Spindle. Color (upper surface): 144C. Color (lower surface): 145C.

*Seed.*—Amount: Sparse, varies between 0 and 20 seeds. Dimensions: 3 mm in length and 2 mm in width. Color: 202A. Shape: Oval and flattened. Surface: Crinkled.

The invention claimed is:

1. A new and distinct cultivar of *Dianthus* plant named 'WP10 HEL01' as described and illustrated herein.

* * * * *